United States Patent
Tan et al.

(10) Patent No.: US 10,994,000 B2
(45) Date of Patent: May 4, 2021

(54) RABBIT COCCIDIOSIS VACCINE AND APPLICATION THEREOF

(71) Applicant: Foshan Standard Bio-Tech Co., Ltd., Foshan (CN)

(72) Inventors: Zhijian Tan, Foshan (CN); Yabiao Weng, Foshan (CN); Lidan Liu, Foshan (CN); Yuan Liu, Foshan (CN); Xinqiu Wang, Foshan (CN); Li Zeng, Foshan (CN); Shifeng Huang, Foshan (CN); Yijuan Huang, Foshan (CN); Yaoyao Ou, Foshan (CN)

(73) Assignee: Foshan Standard Bio-Tech Co., Ltd., Foshan (CN)

( * ) Notice: Subject to any disclaimer, the term of this patent is extended or adjusted under 35 U.S.C. 154(b) by 0 days.

(21) Appl. No.: 16/488,034

(22) PCT Filed: Aug. 10, 2018

(86) PCT No.: PCT/CN2018/099991
§ 371 (c)(1),
(2) Date: Aug. 22, 2019

(87) PCT Pub. No.: WO2019/218502
PCT Pub. Date: Nov. 21, 2019

(65) Prior Publication Data
US 2020/0197501 A1 Jun. 25, 2020

(30) Foreign Application Priority Data

May 18, 2018 (CN) .......................... 201810479606.6

(51) Int. Cl.
| | | |
|---|---|---|
| A61K 39/012 | (2006.01) |
| A61K 35/68 | (2006.01) |
| C07K 14/455 | (2006.01) |
| A61K 39/00 | (2006.01) |
| A61P 33/02 | (2006.01) |

(52) U.S. Cl.
CPC ............ *A61K 39/012* (2013.01); *A61K 35/68* (2013.01); *A61P 33/02* (2018.01); *C07K 14/455* (2013.01); *A61K 2039/52* (2013.01); *A61K 2039/542* (2013.01); *A61K 2039/543* (2013.01); *A61K 2039/552* (2013.01)

(58) Field of Classification Search
CPC .......... A61P 33/02; A61P 33/00; A61P 37/04; C12N 1/005; C12N 1/066; C12N 1/10; C12N 3/00; A61K 2039/52; A61K 2039/542; A61K 2039/543; A61K 2039/552; A61K 39/012
See application file for complete search history.

(56) References Cited

U.S. PATENT DOCUMENTS

| | | | | |
|---|---|---|---|---|
| 4,808,404 A | 2/1989 | Bhogal | | |
| 2008/0194006 A1* | 8/2008 | Hutchins | ................. | A61P 33/02 |
| | | | | 435/258.4 |

FOREIGN PATENT DOCUMENTS

| | | |
|---|---|---|
| AU | 618058 | 7/1989 |
| AU | 2838489 A | 7/1989 |
| CN | 106754379 A | 5/2017 |
| DK | 9089 A | 7/1989 |
| EP | 0 325 359 A1 | 7/1989 |
| FI | 1890118 A | 7/1989 |
| JP | 1-190634 A | 7/1989 |
| NO | 890103 L | 7/1989 |
| NZ | 227570 A | 7/1990 |
| PH | 24966 A | 12/1990 |
| PT | 89419 A | 2/1990 |
| ZA | 8900231 B | 10/1989 |

OTHER PUBLICATIONS

Akpo et al. Veterinary Parasitology 184: 73-76, 2012.*
Wang Yun-Zhou et al. Preliminary study of live oocyst vaccine against rabbit coccidiosis. In: Proceedings of the Inaugural Conference of the Rabbit Credit Association of the Chinese Society of Animal Husbandry and Veterinary Medicine and the First Academic Exchanges Conference, p. 78, Feb. 2015—Original.*
Wang Yun-Zhou et al. Preliminary study of live oocyst vaccine against rabbit coccidiosis. In: Proceedings of the Inaugural Conference of the Rabbit Credit Association of the Chinese Society of Animal Husbandry and Veterinary Medicine and yje First Academic Exchanges Conferen, p. 78, Feb. 2015, English translation.*
Drouet-Viard F. Veterinary Res. 26: 216-217, 1995.*
Jing et al. Parasitol. Res. 110: 1495-1500, 2012, abstract.*
Licois et al. Parasitol. Res. 76: 192-198, 1990.*
Tian et al., "Research Status of Rabbit Coccidium Vaccine", Animal Husbandry and Feed Science, 2012, 33(3): pp. 79-80, Abstract Only.

* cited by examiner

*Primary Examiner* — Sarvamangala Devi
(74) *Attorney, Agent, or Firm* — Don D. Cha; HDC Intellectual Property Law, LLP

(57) ABSTRACT

The present invention discloses a rabbit coccidiosis vaccine and application thereof, the vaccine comprises 100 to 800 *Eimeria media*/dose, 200 to 1600 *Eimeria magna*/dose, and 100 to 800 *Eimeria intestinalis*/dose. The composition of the vaccine possesses the characteristics as scientific reasonable, low cost, no drug residue or drug resistance or environmental pollution would occur, good immunogenicity and safe to use. After oral immunization in rabbits, it may effectively resist the infections of $1\times10^5$ *Eimeria media*, $5\times10^4$ *Eimeria magna* and $3\times10^3$ *Eimeria intestinalis*. It also may be used to prepare a pharmaceutical preparation against rabbit coccidiosis.

6 Claims, No Drawings

RABBIT COCCIDIOSIS VACCINE AND APPLICATION THEREOF

TECHNICAL FIELD

The present invention relates to a veterinary biological product and application field thereof, and in particular, to a rabbit coccidiosis vaccine and application thereof.

BACKGROUND

Rabbit coccidiosis is a parasitic disease caused by *Eimeria* (Eimeriidae, Phylum Apicomplexa) that are parasitized in small intestine or biliary epithelial cells of rabbits. Currently, there are 11 types of globally recognized rabbit *Eimeria*. The rabbit coccidiosis may occur in any place where rabbits are bred. Rabbit coccidiosis is listed as one of the second-class animal diseases in China. All rabbit varieties are susceptible to this disease, particularly, the most serious infection and morbidity may occur among the youngest rabbits after being weaned to 3 months old, and the mortality rate is very high. It is a common disease in rabbit breeding production. Rabbits with the disease often have the symptoms such as lassitude, malnutrition, slow growth, and diarrhea, etc., and even acute death may occur. In particular, the post-infection mortality rate in young rabbits is as high as 40% to 70%, which brings great harm to the rabbit breeding industry and seriously hinders its development.

Conventionally, the main prevention method for rabbit coccidiosis is the drug control. At present, there are many kinds of anticoccidial drugs, which have different control effects. As coccidia occurring on other animals, rabbit coccidian is prone to produce drug resistance. The long-term and continuous use of drugs leads to increase serious drug resistance, and turns out to be a decline in therapeutic efficacy of drugs, even total ineffectiveness. Researchers have also found that rabbit coccidia oocysts can be detected in rabbit populations for both poorly conditioned farms and well-managed intensive rabbit farms, no matter the anticoccidial drugs have been used or not. In view of the issue of drug resistance, researchers have been dedicated to the researches on drug resistance of coccidia and research and development of new drugs. Although the development of new drugs can solve the problem of drug resistance, however, with the increased drug resistance of coccidia, the problems such as drug residues, environmental pollution, and harm to human health will undoubtedly bring more difficulties and new challenges to the drugs control. Due to the research and development of new drugs possesses the characteristics as long researching period, high risk, and huge input of funds, resources and manpower, no new anticoccidial drugs have come into the market since the late 1980s up to now.

Therefore, it is a common goal for rabbit breeding enterprises and researchers to find a new method for the prevention of the rabbit coccidiosis. Wherein, the immune prevention is considered as one of the most promising methods and channels to control this disease and a feasible solution to solve the above problems at present.

SUMMARY

In view of the defects described in the above prior art, the object of the present invention is to provide a rabbit coccidiosis vaccine and application thereof for the purpose that to solve the problem of the control of rabbit coccidiosis that mainly depends on drug control in the prior art; and the drug control may often cause the problems such as increased drug resistance of rabbit coccidiosis, drug residues, environmental pollution, and harm to human health, as well as the research and development of new drugs taking a long time, having high risk and high economic cost.

In order to achieve the above object, the present invention adopts the following technical solutions: A rabbit coccidiosis vaccine, wherein said vaccine comprises: 100 to 800 *Eimeria media*/dose, 200 to 1600 *Eimeria magna*/dose, and 100 to 800 *Eimeria intestinalis*/dose.

The rabbit coccidiosis vaccine comprises 300 *Eimeria media*/dose, 600 *Eimeria magna*/dose, and 600 *Eimeria intestinalis*/dose.

In the rabbit coccidiosis vaccine, the *Eimeria media* is a precocious strain of *Eimeria media*, the *Eimeria magna* is a precocious strain of *Eimeria magna*, and the *Eimeria intestinalis* is a precocious strain of *Eimeria intestinalis*.

In the application of the rabbit coccidiosis vaccine, the vaccine is used to immunize rabbit *Eimeria*. In the application of the rabbit coccidiosis vaccine, the rabbit *Eimeria* comprises *Eimeria media*, *Eimeria magna* and *Eimeria intestinalis*.

In the application of the rabbit coccidiosis vaccine, the vaccine is suitable for oral immunization in rabbits aged from 25 to 90 days.

Beneficial Effects

The invention provides a rabbit coccidiosis vaccine and application thereof. The vaccine is made by mixing precocious strains of *Eimeria media*, *Eimeria magna* and *Eimeria intestinalis* at appropriate ratio. The composition possesses the characteristics as scientific reasonable, low cost, no drug residue or drug resistance or environmental pollution would occur, good immunogenicity and safe to use. It may effectively resist the infection of $1\times10^5$ *Eimeria media*, $5\times10^4$ *Eimeria magna* and $3\times10^3$ *Eimeria intestinalis*. It also may be used to prepare a pharmaceutical preparation against rabbit coccidiosis.

DETAILED DESCRIPTION

The present invention provides a rabbit coccidiosis vaccine and application thereof. In order to make the objects, technical solutions and effects of the invention more clear and explicit, the present invention will be further described in detail as follows by the illustration of embodiments. It should be understood that the specific embodiments described herein merely illustrate the present invention and are not intended to limit the present invention.

The present invention provides a rabbit coccidiosis vaccine, comprising: 100 to 800 *Eimeria media*/dose, 200 to 1600 *Eimeria magna*/dose, 100 to 800 *Eimeria intestinalis*/dose. *Eimeria media*, *Eimeria magna* and *Eimeria intestinalis* are widespread and moderately or strongly toxic, and are more harmful to rabbits. The vaccine is obtained by mixing precocious strains of the above three *Eimeria* species that are more harmful to rabbits at a specific ratio. The obtained vaccine has good immunogenicity and is safe to use. The above dose may guarantee the immune effect with low cost, and may control the vaccine response at a low level, thereby to reduce the influence on the production of rabbits. When the values of immune doses of *Eimeria media*, *Eimeria magna*, and *Eimeria intestinalis* are less than the above values, it is unable to provide effective immune protection to rabbits; when the values of immune doses of *Eimeria media*, *Eimeria magna*, and *Eimeria intestinalis* are greater than the above values, the immune response is too strong, which will produce great influence on the production of rabbits.

Preferably, the vaccine comprises 300 *Eimeria media*/dose, 600 *Eimeria magna*/dose, and 600 *Eimeria intestinalis*/dose; applying the above doses may lead to the best immune effect of vaccine, low cost, slight side reactions and low influence on the production of rabbits, thus it is the best ratio.

Preferably, the *Eimeria media* is a precocious strain of *Eimeria media*, the *Eimeria magna* is a precocious strain of *Eimeria magna*, and the *Eimeria intestinalis* is a precocious strain of *Eimeria intestinalis*. The precocious strains are less pathogenic than the original strains, but may retain immunogenicity, so the immune effect of vaccines is fully guaranteed; moreover, it is safer to use and avoiding potential poisoning threats and excessive damage to the intestinal tracts of rabbits during use that may cause the harms such as the reduction of the production performance and increase of the breeding costs, etc.

In the applications of the rabbit coccidiosis vaccine, the vaccine is used for the immunization of rabbit *Eimeria*.

Specifically, the rabbit *Eimeria* comprises *Eimeria media*, *Eimeria magna*, and *Eimeria intestinalis*; the vaccine may effectively resist the infection of $1\times10^5$ *Eimeria media*, $5\times10^4$ *Eimeria magna* and $3\times10^3$ *Eimeria intestinalis*.

Specifically, the vaccine is applied to rabbits of various strains or for different purposes, including New Zealand rabbits, Hyla rabbits, REX rabbits, California rabbits, meat rabbits, long-haired rabbits, pet rabbits, and experimental rabbits, etc.

Specifically, the vaccine is suitable for oral immunization in rabbits aged from 25 to 90 days; the vaccine is orally immunized, including mixing feed immunized, drinking water immunized or intranasal immunized, etc.

Example 1 Formulation of Rabbit Coccidiosis Vaccine

The sporulated oocysts of *Eimeria media*, *Eimeria magna*, and *Eimeria intestinalis* were counted by a blood counting chamber, respectively, and the concentrations were obtained. The required volume of coccidial oocysts of each component was calculated according to the ratios shown in Table 1 and placed in a clean container successively, then preservation solution was added and stirred to obtain the oocyst solution of the mixed strains.

TABLE 1

Ratio of components of rabbit coccidiosis vaccine.

|  | *Eimeria media* (pcs/dose) | *Eimeria magna* (pcs/dose) | *Eimeria intestinalis* (pcs/dose) |
| --- | --- | --- | --- |
| Ratio 1 | 100 | 200 | 800 |
| Ratio 2 | 800 | 200 | 100 |
| Ratio 3 | 300 | 600 | 600 |
| Ratio 4 | 500 | 500 | 500 |
| Ratio 5 | 100 | 1600 | 100 |
| Ratio 6 | 400 | 1200 | 400 |

Example 2

50 normal-class rabbits aged from 25-90 days without coccidiosis tested by fecal examination were divided into 10 groups, 5 in each group. The rabbits in each group were evenly distributed according to the age in days. Among them, groups 1, 2 and 3 were immunized and challenged groups of ratio 1, and groups 4, 5 and 6 were immunized and challenged groups of ratio 2, and groups 7, 8 and 9 were non-immunized and challenged groups, and group 10 was non-immunized and non-challenged group. Rabbits in the 10 groups were separately fed under the same conditions, and the rabbits were weighed and challenged on the 14th day by orally immunized with the corresponding vaccines. Rabbits in the groups 1, 4 and 7 were orally challenged by $1\times10^5$ *Eimeria media* sporulated oocysts/rabbit; rabbits in the groups 2, 5 and 8 were orally challenged by $5\times10^4$ *Eimeria magna* sporulated oocysts/rabbit; and rabbits in the groups 3, 6 and 9 were orally challenged by $3\times10^3$ *Eimeria intestinalis* sporulated oocysts/rabbit, and then observed for 12 days. The feces on the 5th and 6th days after challenge on the groups 1, 4 and 7 were collected and the number of oocysts was calculated, the feces on the 8th and 9th days after challenge on the groups 2, 5 and 8 were collected and the number of oocysts was calculated, and the feces on the 11th and 12th days after challenge on the groups 3, 6 and 9 were collected and the number of oocysts was calculated. On the 12th day after challenge, the body weights of rabbits in each group were weighed and the relative weight gain rate was calculated. The average relative weight gain rates and the relative decrease rates of OPG (oocysts per gramme) among different groups were compared.

The groups of ratio 3 and ratio 4, ratio 5 and ratio 6 as the combined immunized group were tested in two separate experiments according to the same test method described above.

TABLE 2

The weight gains in various groups at ratio 1 and ratio 2

| Group | Ratio of strains (media: magna: intestinalis) | Challenged type | Number of rabbits (n) | Average weight before immunization/g | Average weight before challenge/g | Average weight gain after immunization a/g | Average rate of relative weight gain a/% | Average weight after challenge/g | Average weight gain after challenge b/g | Average rate of relative weight gain b/% | Mortality/% |
| --- | --- | --- | --- | --- | --- | --- | --- | --- | --- | --- | --- |
| Ratio 1: immunized and challenged group | 100: 200: 800 | media magna intestinalis | 5 5 5 | 1062.6 981.3 917.5 | 1441.3 1341.6 1240.5 | 378.7 360.3 323 | 97.2 92.5 82.9 | 1792.7 1676.4 1595.3 | 351.4 334.8 354.8 | 72 68.6 72.7 | 0 0 0 |
| Ratio 2: immunized and challenged group | 800: 200: 100 | media magna intestinalis | 5 5 5 | 1035.3 819.3 918 | 1359.4 1182 1289.3 | 324.1 362.7 371.3 | 83.2 93.1 95.3 | 1765 1523.2 1584.1 | 405.6 341.2 294.8 | 83.1 69.9 60.4 | 0 0 0 |
| Non-immunized and challenged group | — | media magna intestinalis | 5 5 5 | 933.9 789.7 821.2 | 1324.4 1178.8 1208.3 | 390.5 389.1 387.1 | 100.9 99.9 99.4 | 1565.5 1384.3 1397.2 | 241.1 205.5 188.9 | 49.4 42.1 38.7 | 0 0 0 |

TABLE 2-continued

The weight gains in various groups at ratio 1 and ratio 2

| Group | Ratio of strains (media: magna: intestinalis) | Challenged type | Number of rabbits (n) | Average weight before immunization/g | Average weight before challenge/g | Average weight gain after immunization a/g | Average rate of relative weight gain a/% | Average weight after challenge/g | Average weight gain after challenge b/g | Average rate of relative weight gain b/% | Mortality/% |
|---|---|---|---|---|---|---|---|---|---|---|---|
| Non-immunized and non-challenged group | — | — | 5 | 977.7 | 1367.3 | 389.6 | — | 1855.4 | 488.1 | — | 0 |

Note: In table 2, "media" represented *Eimeria media*; "magna" represented *Eimeria magna*; "intestinalis" represented *Eimeria intestinalis*; "a" indicated the data of weight gain on the 14th day after immunization; "b" indicated the data of weight gain on the 12th day after challenge.

TABLE 3

The weight gains in various groups at ratio 3 and ratio 4

| Group | Ratio of strains (media: magna: intestinalis) | Type of challenge | Number of rabbits (n) | Average weight before immunization/g | Average weight before challenge/g | Average weight gain after immunization a/g | Average rate of relative weight gain a/% | Average weight after challenge/g | Average weight gain after challenge b/g | Average rate of relative weight gain b/% | Mortality/% |
|---|---|---|---|---|---|---|---|---|---|---|---|
| Ratio 3: immunized and challenged group | 300: 600: 600 | media | 5 | 928.5 | 1317.6 | 389.1 | 93.4 | 1642.2 | 324.6 | 77.1 | 0 |
| | | magna | 5 | 877.0 | 1263.2 | 386.2 | 92.7 | 1549.9 | 286.7 | 68.1 | 0 |
| | | intestinalis | 5 | 861.9 | 1250.6 | 388.7 | 93.3 | 1491 | 240.4 | 57.1 | 0 |
| Ratio 4: immunized and challenged group | 500: 500: 500 | media | 5 | 941.2 | 1314.1 | 372.9 | 89.5 | 1641.2 | 327.1 | 77.7 | 0 |
| | | magna | 5 | 887.1 | 1265.4 | 378.3 | 90.8 | 1555.9 | 290.5 | 69.0 | 0 |
| | | intestinalis | 5 | 963.1 | 1338.5 | 375.4 | 90.1 | 1559.9 | 221.4 | 52.6 | 0 |
| Non-immunized and challenged group | — | media | 5 | 884.3 | 1295.9 | 411.6 | 98.8 | 1497.1 | 201.2 | 47.8 | 0 |
| | | magna | 5 | 969.3 | 1396.7 | 427.4 | 102.6 | 1568 | 171.3 | 40.7 | 0 |
| | | intestinalis | 5 | 757.2 | 1171.3 | 414.1 | 99.4 | 1303.9 | 132.6 | 31.5 | 0 |
| Non-immunized and non-challenged group | — | — | 5 | 906.3 | 1322.9 | 416.6 | — | 1743.9 | 421.0 | — | 0 |

Note: In table 3, "media" represented *Eimeria media*; "magna" represented *Eimeria magna*; "intestinalis" represented *Eimeria intestinalis*; "a" indicated the data of weight gain on the 14th day after immunization; "b" indicated the data of weight gain on the 12th day after challenge.

TABLE 4

The weight gains in various groups at ratio 5 and ratio 6

| Group | Ratio of strains (media: magna: intestinalis) | Type of challenge | Number of rabbits (n) | Average weight before immunization/g | Average weight before challenge/g | Average weight gain after immunization a/g | Average rate of relative weight gain a/% | Average weight after challenge/g | Average weight gain after challenge b/g | Average rate of relative weight gain b/% | Mortality/% |
|---|---|---|---|---|---|---|---|---|---|---|---|
| Ratio 5: immunized and challenged group | 100: 1600: 100 | media | 5 | 937.6 | 1332.6 | 395 | 92.8 | 1659.5 | 326.9 | 72.3 | 0 |
| | | magna | 5 | 813.2 | 1155.8 | 342.6 | 80.5 | 1499 | 343.2 | 78 | 0 |
| | | intestinalis | 5 | 1002.2 | 1401.8 | 399.6 | 93.9 | 1609.5 | 207.7 | 47.2 | 0 |
| Ratio 6: immunized and challenged group | 400: 1200: 400 | media | 5 | 741.2 | 1097 | 355.8 | 83.6 | 1441.1 | 344.1 | 78.2 | 0 |
| | | magna | 5 | 959.1 | 1304.7 | 345.6 | 81.2 | 1631.6 | 326.9 | 74.3 | 0 |
| | | intestinalis | 5 | 1014.9 | 1375.8 | 360.9 | 84.8 | 1626.2 | 250.4 | 56.9 | 0 |

TABLE 4-continued

The weight gains in various groups at ratio 5 and ratio 6

| Group | Ratio of strains (media: magna: intestinalis) | Type of challenge | Number of rabbits (n) | Average weight before immunization/ g | Average weight before challenge/ g | Average weight gain after immunization a/g | Average rate of relative weight gain a/% | Average weight after challenge/ g | Average weight gain after challenge b/g | Average rate of relative weight gain b/% | Mortality/% |
|---|---|---|---|---|---|---|---|---|---|---|---|
| Non-immunized and challenged | — | media | 5 | 984.5 | 1416.5 | 432 | 101.5 | 1629.5 | 213 | 48.4 | 0 |
|  |  | magna | 5 | 1004.4 | 1425.3 | 420.9 | 98.9 | 1606.1 | 180.8 | 41.1 | 0 |
|  |  | intestinalis | 5 | 918.3 | 1360.5 | 442.2 | 103.9 | 1500 | 139.5 | 31.7 | 0 |
| Non-immunized and non-challenged group | — | — | 5 | 837.9 | 1263.5 | 425.6 | — | 1703.5 | 440 | — | 0 |

Note: In table 4, "media" represented *Eimeria media*; "magna" represented *Eimeria magna*; "intestinalis" represented *Eimeria intestinalis*; "a" indicated the data of weight gain on the 14th day after immunization; "b" indicated the data of weight gain on the 12th day after challenge.

TABLE 5

Counting results of oocysts in various groups at ratio 1 and ratio 2

| Group | Ratio of strains (media: magna: intestinalis) | Type of challenge | OPG value/ piece/g feces | OPG decrease rate/% | Oocyst production/ten thousand | Relative decrease rate of oocysts/% |
|---|---|---|---|---|---|---|
| Ratio 1: immunized and challenged group | 100: 200: 800 | media | 506000 | 80.9 | 1762.1 | 79.5 |
|  |  | magna | 526500 | 54.5 | 2468.9 | 53.0 |
|  |  | intestinalis | 3934500 | 64.2 | 4485.1 | 62.2 |
| Ratio 2: immunized challenged group | 800: 200: 100 | media | 190750 | 92.8 | 862.7 | 90.0 |
|  |  | magna | 539150 | 53.4 | 2453.1 | 53.3 |
|  |  | intestinalis | 5550000 | 49.5 | 6134.4 | 48.3 |
| Non-immunized and challenged group | — | media | 2649000 | — | 8595.5 | — |
|  |  | magna | 1157000 | — | 5252.9 | — |
|  |  | intestinalis | 10990000 | — | 11865.3 | — |

Note: In table 5, "media" represented *Eimeria media*; "magna" represented *Eimeria magna*; "intestinalis" represented *Eimeria intestinalis*.

TABLE 6

Counting results of oocysts in various groups at ratio 3 and ratio 4

| Group | Ratio of strains (media: magna: intestinalis) | Type of challenge | OPG value/ piece/g feces | OPG decrease rate/% | Oocyst production/ten thousand | Relative decrease rate of oocysts/% |
|---|---|---|---|---|---|---|
| Ratio 3: immunized and challenged group | 300: 600: 600 | media | 277550 | 89.8 | 929.9 | 88.5 |
|  |  | magna | 483200 | 57.2 | 2632.8 | 52.4 |
|  |  | intestinalis | 5557000 | 56.0 | 4134.6 | 55.6 |
| Ratio 4: immunized challenged group | 500: 500: 500 | media | 272100 | 90.0 | 789.6 | 90.2 |
|  |  | magna | 479800 | 57.5 | 2371.5 | 57.1 |
|  |  | intestinalis | 5822500 | 53.9 | 4339.4 | 53.4 |
| Non-immunized and challenged group | — | media | 2721000 | — | 8057.4 | — |
|  |  | magna | 1129000 | — | 5527.9 | — |
|  |  | intestinalis | 12630000 | — | 9312.1 | — |

Note: In table 6, "media" represented *Eimeria media*; "magna" represented *Eimeria magna*; "intestinalis" represented *Eimeria intestinalis*.

TABLE 7

Counting results of oocysts in various groups at ratio 5 and ratio 6

| Group | Ratio of strains (media: magna: intestinalis is) | Type of challenge | OPG value/ piece/g feces | OPG decrease rate/% | Oocyst production/ten thousand | Relative decrease rate of oocysts/% |
|---|---|---|---|---|---|---|
| Ratio 5: immunized and challenged group | 100: 1600: 100 | media magna intestinalis | 500300 359000 4503100 | 81.8 63.2 51.0 | 1559.2 1970.7 5697.5 | 80.5 62.4 50.6 |
| Ratio 6: immunized challenged group | 400: 1200: 400 | media magna intestinalis | 244650 385300 4080300 | 91.1 60.5 55.6 | 1839.1 2101.8 4867.1 | 77.0 59.9 57.8 |
| Non-immunized and challenged group | — | media magna intestinalis | 2749000 975500 9190000 | — — — | 7996.3 5241.3 11533.4 | — — — |

Note: In table 7, "media" represented *Eimeria media*; "magna" represented *Eimeria magna*; "intestinalis" represented *Eimeria intestinalis*.

The test results were shown in Tables 2 to 7. Before the challenge, the average rates of relative weight gain of various groups immunized with the vaccines at ratios 1 to 6 were 90.7%, 90.5%, 93.1%, 90.1%, 89.1%, 83.2. %, respectively, and no death occurred in rabbits of each immunized group. After the challenge, the rates of relative weight gains in various groups challenged with *Eimeria media*, *Eimeria magna* and *Eimeria intestinalis* at the ratio 1 were 76.0%, 68.6%, and 72.7%, respectively; likewise, the rates of relative weight gains in various vaccine immunized groups at the ratio 2 were 83.1%, 69.9%, and 60.4%, respectively; the rates of relative weight gains in various vaccine immunized groups at the ratio 3 were 77.1%, 68.1%, and 57.1%, respectively; the rates of relative weight gains in various vaccine immunized groups at the ratio 4 were 77.7%, 69.0%, and 52.6%, respectively; the rates of relative weight gains in various vaccine immunized groups at the ratio 5 were 72.3%, 78.0%, and 47.2%, respectively; the rates of relative weight gains in various vaccine immunized groups at the ratio 6 were 78.2%, 74.3%, and 56.9%, respectively.

After challenge, the relative OPG decrease rates and the relative decrease rates of oocysts in various groups challenged with *Eimeria media*, *Eimeria magna* and *Eimeria intestinalis* at the ratio 1 were 80.9%, 54.5%, 64.2% and 79.5%, 53.0%, 62.2%, respectively; those in various groups at the ratio 2 were 92.8%, 53.4%, 49.5% and 90.0%, 53.3%, 48.3%, respectively; those in various groups at the ratio 3 were 89.8%, 57.2%, 56.0% and 88.5%, 52.4%, 55.6%, respectively; those in various groups at the ratio 4 were 90.0%, 57.5%, 53.9% and 90.2%, 57.1%, 53.4%, respectively; those in various groups at the ratio 5 were 81.8%, 63.2%, 51.0%, and 80.5%, 62.4%, and 50.6%, respectively; those in various groups at the ratio 6 were 91.1%, 60.5%, 55.6%, and 77.0%, 59.9%, and 57.8%, respectively.

Apparently, the rate of relative weight gains in each group immunized with the vaccines at ratios 1 to 6 was significantly higher than that in the corresponding non-immunized and challenged group, specifically, the rate of relative weight gains at the ratio 1 was higher than that in the corresponding non-immunized and challenged group by 22.6% to 34.0%; the rate of relative weight gains at the ratio 2 was higher than that in the corresponding non-immunized and challenged group by 21.7% to 33.7%; the rate of relative weight gains at the ratio 3 was higher than that in the corresponding non-immunized and challenged group by 25.6% to 29.3%; the rate of relative weight gains at the ratio 4 was higher than that in the corresponding non-immunized and challenged group by 21.1% to 29.9%; the rate of relative weight gains at the ratio 5 was higher than that in the corresponding non-immunized and challenged group by 15.5% to 36.9%; the rate of relative weight gains at the ratio 6 was higher than that in the corresponding non-immunized and challenged group by 25.2% to 36.9%. Moreover, the relative OPG decrease rates and the relative decrease rates of oocysts in various immunized and challenged groups after challenged with *Eimeria media*, *Eimeria magna* and *Eimeria intestinalis* were higher than 77.0% 52.4% and 48.3% respectively, indicating that various groups at the ratios 1 to 6 achieved a good immune effect and had a low effect on the weight gain of rabbits, and it was effective to resist the challenges of *Eimeria media*, *Eimeria magna* and *Eimeria intestinalis* at high doses.

Further, before challenge, the rate of relative weight gains in the group immunized with the vaccines at ratio 3 was significantly superior to that in the groups immunized with vaccines at other five ratios; after challenge, the rates of relative weight gains and the relative OPG decrease rates in the groups immunized with the vaccines at ratios 3, 4 and 6 were superior to those in the groups immunized with the vaccines at ratios 1, 2 and 5. Thus, by combining the influence of vaccines on the weight gains of rabbits during immunization with the relative OPG decrease rates and the relative decrease rates of oocysts after challenge, the applicant concluded that the optimal ratio of the vaccine was the ratio 3, that is, when each dose of vaccine contained 300 sporulated oocysts of *Eimeria media* precocious strain, 600 sporulated oocysts of *Eimeria magna* precocious strain and 600 sporulated oocysts of *Eimeria intestinalis* precocious strain, it had the slightest effect on the rabbit's body during the immunization and provided relatively strong protection effect of immunization after challenge.

The test results of rabbits in other ages in days also showed that vaccines with ratios 1 to 6 were safe to use, and the ratio 3 was the optimal ratio.

It should be understood that those skilled in the art may make equivalent substitutions or changes to the technical solutions and concepts according to the present invention, and all such changes or substitutions shall fall into the scope of protection of the appended claims.

The invention claimed is:

1. A rabbit coccidiosis vaccine, wherein the rabbit coccidiosis vaccine consists of 100 to 800 sporulated cysts of *Eimeria media* per dose, 200 to 1600 sporulated cysts of *Eimeria magna* per dose, and sporulated cysts of *Eimeria intestinalis* per dose, and wherein the *Eimeria media* is a precocious strain of *Eimeria media*, the *Eimeria magna* is a precocious strain of *Eimeria magna*, and the *Eimeria intestinalis* is a precocious strain of *Eimeria intestinalis*, and the rabbit coccidiosis vaccine is suitable for immunizing rabbits aged from 25 to 90 days.

2. The rabbit coccidiosis vaccine according to claim 1, wherein the vaccine comprises 300 sporulated oocysts of the *Eimeria media* per dose, 600 sporulated oocysts of the *Eimeria magna* per dose, and 600 sporulated oocysts of the *Eimeria intestinalis* per dose.

3. The rabbit coccidiosis vaccine according to claim 1, wherein the rabbit coccidiosis vaccine is suitable for oral immunization in rabbits, and the oral immunization comprises mixing feed immunization and drinking water immunization.

4. The rabbit coccidiosis vaccine according to claim 1, wherein the rabbit coccidiosis vaccine is suitable for intranasal immunization.

5. A method of immunization of rabbits aged from 25 to 90 days against coccidiosis caused by *Eimeria media*, *Eimeria magna* or *Eimeria intestinalis*, the method comprising oral administration to said rabbits the rabbit coccidiosis vaccine of claim 1.

6. The method of claim 5, wherein the immunization comprises mixing feed immunization and drinking water immunization.

* * * * *